United States Patent [19]
Bellhouse et al.

[11] Patent Number: 5,254,259
[45] Date of Patent: Oct. 19, 1993

[54] METHOD AND APPARATUS FOR EFFECTING THE TRANSFER OF HEAT OR MASS THROUGH A MEMBRANE INVOLVING THE USE OF VORTICES

[76] Inventors: Brian J. Bellhouse, The Lodge, North Street, Islip, Oxfordshire OX5 2SQ; Ian J. Sobey, 11 Wyndam Way, Oxford OX2 8DF, both of United Kingdom

[21] Appl. No.: 829,089
[22] PCT Filed: Aug. 17, 1990
[86] PCT No.: PCT/GB90/01301
§ 371 Date: Feb. 13, 1992
§ 102(e) Date: Feb. 13, 1992

[30] Foreign Application Priority Data

Aug. 17, 1989 [GB] United Kingdom ............... 8918772
Jan. 25, 1990 [GB] United Kingdom ............... 9001702

[51] Int. Cl.$^5$ .................... B01D 61/00; B01D 61/28
[52] U.S. Cl. .................... 210/650; 210/320; 210/321.75; 210/356
[58] Field of Search ............ 210/320, 356, 321.72, 210/321.75, 321.84, 500.21, 650, 321.6, 456, 646; 422/45, 46, 48, 228

[56] References Cited

U.S. PATENT DOCUMENTS

| | | | |
|---|---|---|---|
| 836,386 | 11/1906 | Keegan | 210/320 |
| 4,357,239 | 11/1982 | Bellhouse et al. | 210/321.72 |
| 4,383,921 | 5/1983 | Bellhouse et al. | 210/321.72 |
| 4,624,778 | 11/1986 | Clermont et al. | 210/321.72 |
| 4,636,309 | 1/1987 | Bellhouse | 210/356 |
| 4,636,310 | 1/1987 | Bellhouse | 210/321.72 |
| 4,895,652 | 1/1990 | Cornelissen | 210/320 |
| 5,120,445 | 6/1992 | Colman | 210/456 |
| 5,167,817 | 12/1992 | Bellhouse | 210/321.75 |

FOREIGN PATENT DOCUMENTS 2319397 2/1977 France .
8904197 5/1989 PCT Int'l Appl. .
2009618 6/1979 United Kingdom .

OTHER PUBLICATIONS

Ian J. Sobey, Chemical Engineering Science, vol. 40, No. 11, pp. 2129-2134 (1985).
Ian J. Sobey, J. Fluid Mechanics, vol. 125, pp. 359-373 (1982).
Ian J. Sobey, J. Fluid Mechanics, vol. 151, pp. 395-426 (1985).

*Primary Examiner*—Robert A. Dawson
*Assistant Examiner*—Sun Uk Kim
*Attorney, Agent, or Firm*—Baker & Daniels

[57] ABSTRACT

Standing vortices are formed in a liquid flowing with a reversing but mean flow through a conduit, divided into a series of chambers with narrow inlet and outlets by appropriate selection of the chamber aspect ratio, Reynolds number and Strouhal number.

15 Claims, 6 Drawing Sheets

METHOD AND APPARATUS FOR EFFECTING THE TRANSFER OF HEAT OR MASS THROUGH A MEMBRANE INVOLVING THE USE OF VORTICES

A first aspect of the invention relates to a method and apparatus for effecting transfer of heat or mass to or from a fluid, which is usually a liquid, through a transfer membrane. Such technique is used in blood oxygenators and dialysers, in which case one fluid is blood and the other is oxygen or dialysate. Alternatively such apparatus may be used for filtering, for example components such as plasma from whole blood, or for introducing or removing material into or from a bioreactor.

In practice the efficiency of the transfer across the membrane is limited to the extent to which the total volume of fluid can be brought into close proximity with the membrane. One solution to this problem is disclosed in GB-A-1442754 and EP-A-0111423 and involves passing one fluid with a pulsatile, and preferably reversing, flow, but with a mean flow, through a conduit, a wall of which is provided with a regularly longitudinally repeating array of hollows, such as dimples or transverse furrows, as a result of which vortices are set up in the fluid in the hollows. In practice, the geometry has been such that one vortex has been formed in each hollow. When reversing flow, which is preferred, is used, the vortices, which have all been rotating in the same sense, are shed from the hollows into the mainstream flow and decay when the flow in one direction decelerates, and are reestablished in the hollows, but with rotation in the opposite sense, when the flow has reversed and accelerates in the opposite direction along the conduit. This repeated decay and reversal in the direction of rotation of the vortices is less efficient in mixing the fluid, than if the vortices were maintained continuously.

The production of vortices in a liquid may also be used according to a second aspect to promote thorough mixing of the components of a fluid, for example to promote a chemical reaction between components; or to promote contact between the fluid and a component such as an affinity ligand immobilised on a support.

In accordance with the present invention, in a method utilising vortices in a fluid, the fluid is passed with reversing, but mean, flow through a conduit comprising at least one chamber defined between two side walls, the chamber being provided at its ends spaced along the conduit with a restricted inlet and a restricted outlet, the Reynolds and Strouhal numbers of the fluid system, and the aspect ratio of the length of the chamber to the width of the chamber between the two walls being such that at least three vortices are set up in a standing pattern along the chamber with adjacent vortices rotating in opposite senses about axes perpendicular to the length and width of the chamber and with mainstream flow of the fluid passing along the chamber and sinuously around the vortices alternately between a vortex and different one of the walls, reversal of the flow direction reinforcing the vortices so that each continues to rotate in the same sense but with the sinuous flow now passing around each vortex and the opposite wall.

The inlet and outlet will be at the upstream and downstream ends, respectively, of the chambers as considered in the direction of mean flow, although the nominal outlet will act as an inlet during that part of each flow cycle when the flow is in the reverse direction to the mean flow.

This technique is an extension of the previous technology, in effect by extending the dimensions of the hollows along and across the conduit and providing particular parameters, including the sizes and positions of the restricted inlet and outlet to the chamber, the stroke and frequency of the pump or pumps producing the reversing but mean flow, and the viscosity of the fluid, all of which are in practice determined by selected Reynolds and Strouhal numbers and chamber aspect ratio, so that a virtual standing wave pattern is set up in the chamber with three or more continually rotating vortices. These vortices will oscillate, with adjacent vortices out of phase with one another, to and fro between the opposed walls of the chamber, as the flow reverses, but their positions along the chamber will remain substantially constant. This resonant condition can be tuned by adjustment of the pump stroke and frequency. This leads to excellent and continuous mixing of the fluid and consequently desirably good contact between the fluid and transfer membrane if at least one of the walls is at least partly formed by a transfer membrane for heat or mass transfer in accordance with the first aspect. It is expected that, as compared with the previous vortex mixing technology, the pump or pumps will operate with smaller volumes and higher frequencies, and there will be higher Reynolds and Strouhal numbers in the system according to the invention.

If the inlet and outlet are both provided adjacent to the same wall of the conduit, an even number of 4, 6, 8 etc. vortices may be generated in the chamber. On the other hand, if the inlet and outlet are provided adjacent to opposite walls, an odd number of 3, 5, 7 etc. vortices may be established.

The invention also includes apparatus for carrying out the new method, the apparatus comprising a conduit, means for passing fluid through the conduit with a reversing, but mean, flow, the conduit incorporating at least one chamber defined between two side walls at least one of which may be at least partly formed by a transfer membrane, and the chamber being laterally restricted at opposite ends to provide an inlet and an outlet.

Each end of the chamber may be provided by a deflector surface which extends from one side wall, across the width of the chamber towards, but terminating short of, the opposite side wall, thereby forming, adjacent to the opposite wall, the respective inlet or outlet. When, during the flow cycle, fluid enters the chamber through that inlet or outlet the fluid will be directed along that opposite side wall and the vortex nearest to that end of the chamber will be established between the mainstream flow and the one wall.

There may be a number of the chambers in series along the conduit and the restricted inlet and outlet at the (mean) upstream and downstream ends of each chamber may be provided by deflectors affixed to the walls, or by an integral structure which forms or bears against at least one of the walls. A deflector forming the inlet to one chamber may simultaneously form the outlet to the preceding chamber in the direction of mean flow.

Various configurations are possible. Thus the walls may be substantially planar with the two side walls closely spaced as compared to their lengths and widths. In this case, the deflectors may be provided by rungs of a ladder-like structure, the rungs of which are alternatively offset towards opposite side walls. Alternatively, the arrangement may be axisymmetrical, in which case the side walls may be provided one by a core and the other by a surrounding annular wall, the length of the chamber being in the axial direction and the width in the radial direction.

Some examples of systems utilizing the present invention are illustrated diagrammatically in the accompanying drawings, in which.

The FIGS. 1 to 5 illustrate the principles behind the invention.

Figure 1:
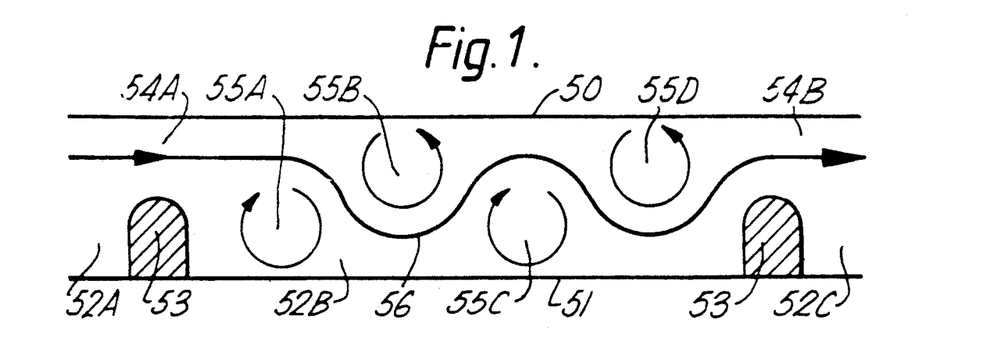
Figure 2:
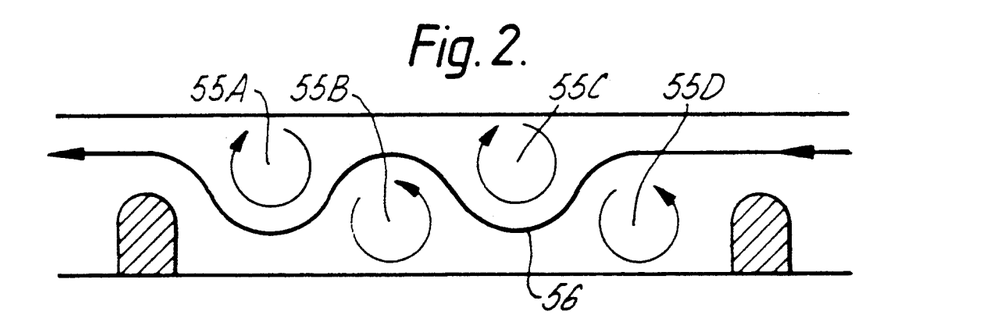

FIGS. 1 and 2 show a conduit defined between two walls 50,51, of which at least one may be a transfer membrane. A series of chambers 52A,52B and 52C are defined along the conduit and separated by deflectors 53 which restrict the width of the conduit and provide with the wall 50, passageways 54A and 54B. Pumps are provided at each end of the conduit to pass fluid with a reversing but mean flow along the conduit. If the mean flow is from left to right in the figures, the passageway 54A will be a nominal outlet from the chamber 52A and a nominal inlet to the chamber 52B, and the passageway 54B will form a nominal outlet from the chamber 52B and a nominal inlet to the chamber 52C.

When the flow is from left to right, as shown in FIG. 1, four vortices 55A,55B,55C and 55D are formed and the main stream flow 56 of the fluid is sinuous around the vortices. When the flow is reversed as shown in FIG. 2, the flow 56 reinforces the vortices, which continue to rotate in the same direction, but the flow now passes around the opposite side of each vortex which has now been displaced towards the opposite one of the walls 50,51.

The continuous rotation of the vortices ensures the thorough mixing of the fluid in the conduit and, when the walls 50 and/or 51 are transfer membranes, enhances contact between the fluid and the membrane.

Figure 3:
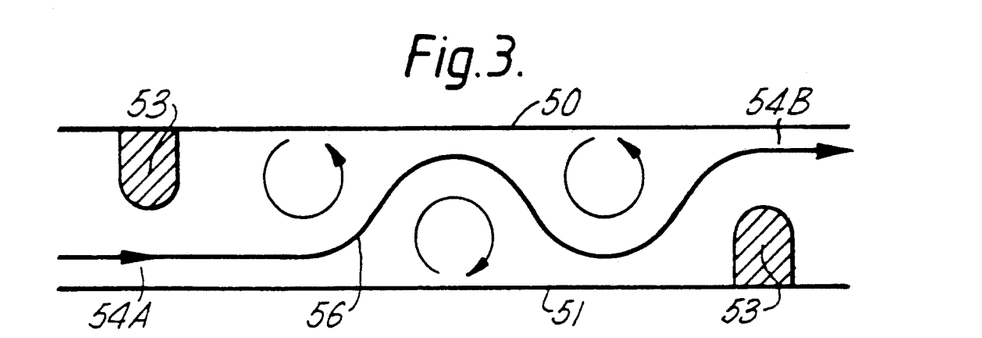
Figure 4:
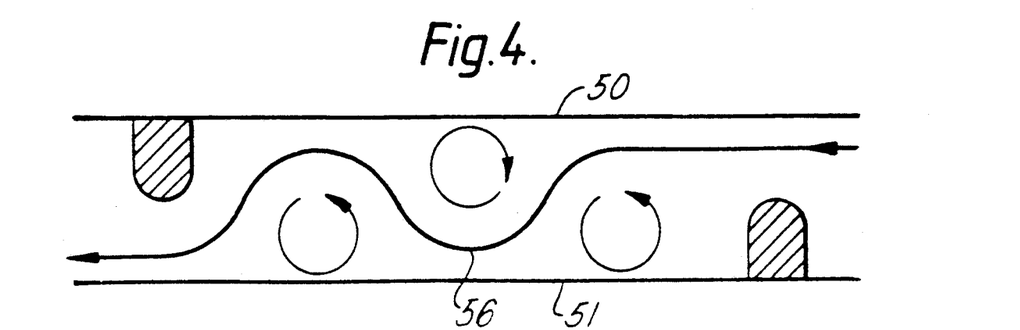

FIGS. 3 and 4 correspond to FIGS. 1 and 2 respectively and show an analagous system in which the deflectors 53 extend alternately from opposite walls 50,51 of the conduit thereby supporting an odd number of vortices 55.

In both cases, analagous vortices will be set up in the adjacent chambers along the conduit.

The walls 50,51 may be planar or the views may be considered to be axial sections, in which case the walls 51 may be formed by central cores of an axisymmetric system, the walls 50 being annular and surrounding the core. The production of the standing pattern of vortices should be analagous in each case.

Figure 5:
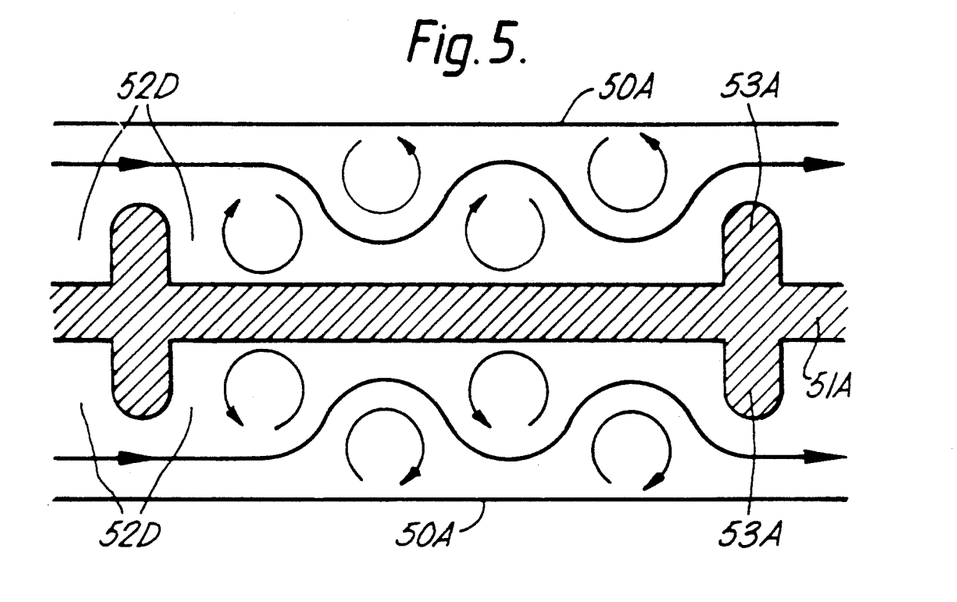

A further option is shown in FIG. 5. In this case pairs of conduits with respective chambers 52D are formed between two walls 50A, at least one of which may be a transfer membrane, and an intermediate dividing wall 51A, with which deflectors 53A are integrally formed. The flow pattern in FIG. 5 corresponds to FIG. 1 but upon reversal the FIG. 2 configuration will obtain in each conduit.

Figure 6:
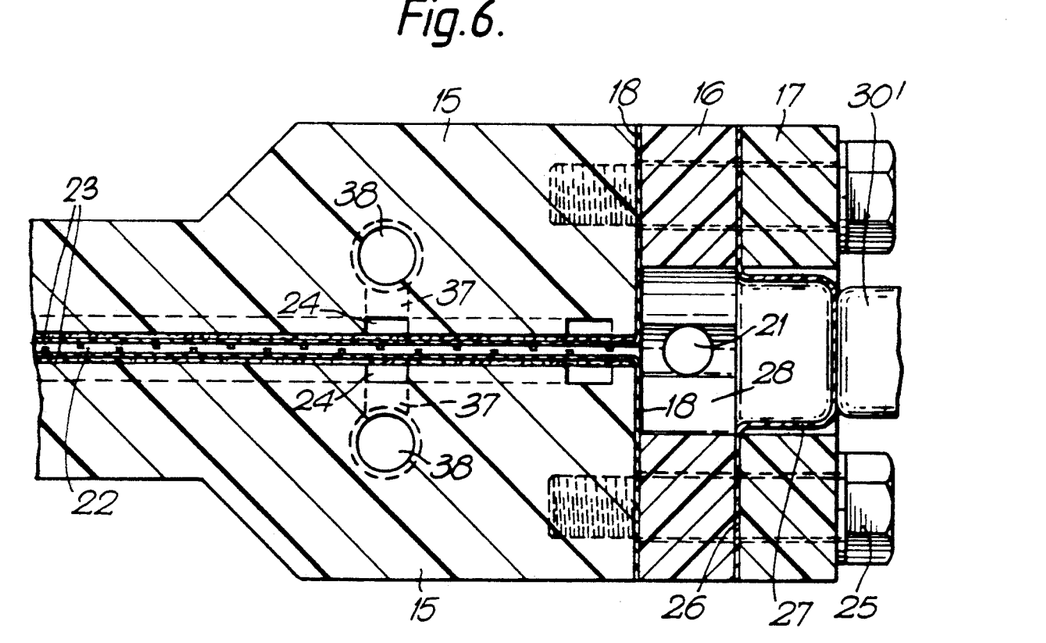
FIG. 6 is a section of part of an apparatus constructed in accordance with the invention.
Figure 7:
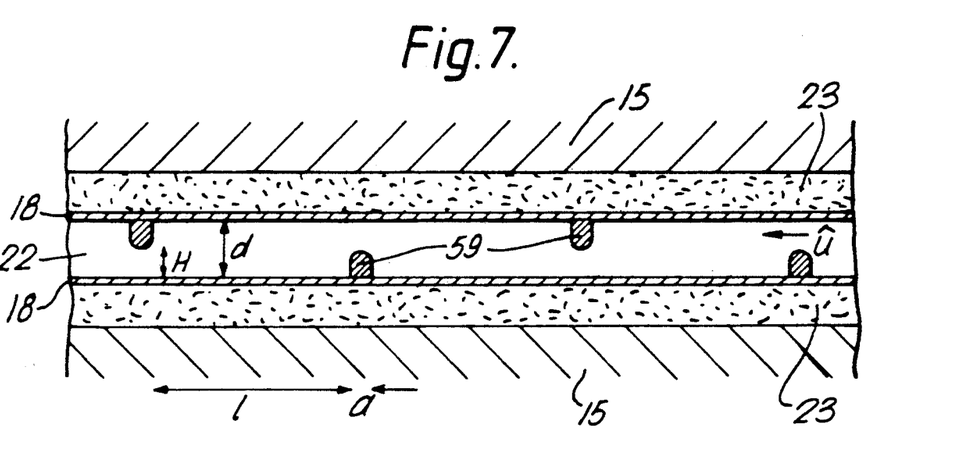
FIG. 7 is an enlargement of a part of FIG. 6.

As shown in FIGS. 6 to 10, the invention can be put into effect by a comparatively simple modification to the apparatus described and illustrated in my WO 89/04197. FIGS. 6 and 7 correspond directly to FIGS. 3 and 6 of the earlier specification, except for the modification, and those reference numerals in FIG. 6 which are common to reference numerals used in FIG. 3 of the earlier specifcation relate to similar parts.

Thus FIG. 6 shows one end of the apparatus comprising similar opposed side plates 15 and pairs of end plates 16 and 17. The side plates are rectangular and elongate and the facing adjacent surfaces of the plates are profiled. Positioned between the two profiled surfaces of the side plates 15 are a pair of membranes 18. Along the longer sides of the plates 15 the membranes 18 are sealed to one another and to the plates 15 by bolts which draw the plates together. There is thus formed between the membranes 18 a central first conduit 22 and, between each membrane 18 and the adjacent surface of the adjacent plate 15, an outer second conduit 23. The profiling of the surfaces of the plates 15 consists of a ladder-like array of channels 24, in communication with the second conduits 23 and leading through ports 37 in the respective plate via a bore 38 to an outlet hose.

At each of the ends of the plates 15, the two plates 16 and 17 are bolted to them by bolts 25 and the ends of the membranes 18 are clamped between the ends of the plates 15 and the end plates 16. Clamped between each of the plates 16 and the adjacent plates 17 is an outwardly extending flange 26 of a flexible diaphragm 27. A manifold 28 in communication with the adjacent end of the central conduit 22, is formed within an open interior of the plate 16 and each of these manifolds 28 is connected through a bore 21 with an external hose. Each diapragm 27 is accommodated within an opening in the respctive plate 17 and is acted upon by a respective pusher 30'. The pushers at the two ends of the apparatus operate out of phase and as each is moved to and fro, liquid is flushed to and fro through the first conduit 22. In order to provide mean flow through the conduit 22, the stroke of one of the pushers 30' may extend further into the respective plates 17 than the other as a result of which there is superimposed upon the reciprocating flow in the first conduit 22, a component which provides a net mean flow through the conduit. A similar mean flow could be achieved by the use of pushers of different cross sectional area instead of, or in addition to, different strokes. Alternatively, if the pushers are similar, mean flow could be provided by the provision of a separate pump, such as a roller pump, in series with the hose leading to the bore 21 at the inlet end of the apparatus.

In the apparatus described in the earlier specification, vortices were set up in the second conduit by preforming the membranes with dimples which nest in respective depressions in the profiling of the plates 15. In contrast, in the present case, standing vortices are set up by the provision in the first conduit 22 of a ladder like structure 57, which holds the two membranes 18 apart. Thus, as shown particularly in FIGS. 8 to 10, the structure 57 has three longitudinal members 58 and a series of rungs 59 which are alternately offset towards opposite faces of the structure so as to form the deflectors 53 of FIG. 3, and to provide the passageways 54 of FIG. 3 as represented by the arrows in FIG. 10.

The arrangement is shown more clearly in FIG. 7, from which it will be apparent that the membranes 18 need not be preformed with any profiling and can be used as flat sheets. This is particularly important when the membranes are delicate microporous membranes for filtration. The membranes could be supported against the profiled surfaces of the plates as described in the earlier specification, the second conduits then being formed by the depressions and interconnecting grooves in the plate surfaces. This arrangement could be used, with appropriate membranes for microfiltration, for example to separate plasma from blood cells or for the concentration of microbial cells, or for low pressure (up to 0.5 bar) ultrafiltration, for example to concentrate an aqueous protein solution. However, for higher pressure ultrafiltration, it may be desirable to support the appropriate membranes over substantially all their surface area. In that case, and as shown in FIG. 7, the second conduits may be formed between the membranes and surfaces of the plates 15 which are substantially planar except for the channels 24, the conduits being filled with a porous foam material to support the membranes 18.

Figure 9:
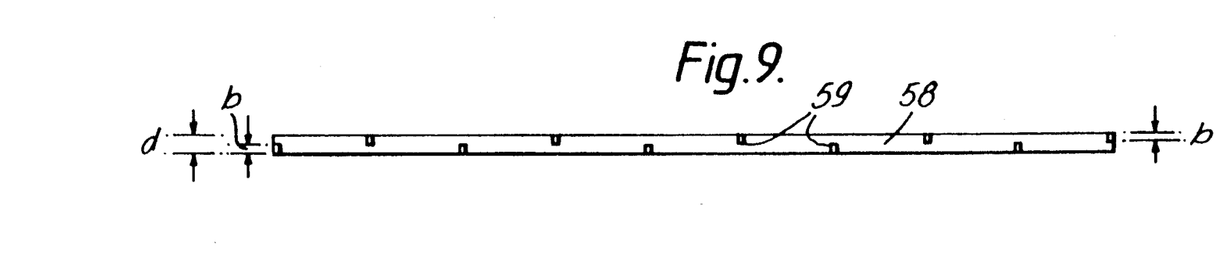
FIG. 9 is a section taken on the line IX—IX in FIG. 8.
Figure 10:
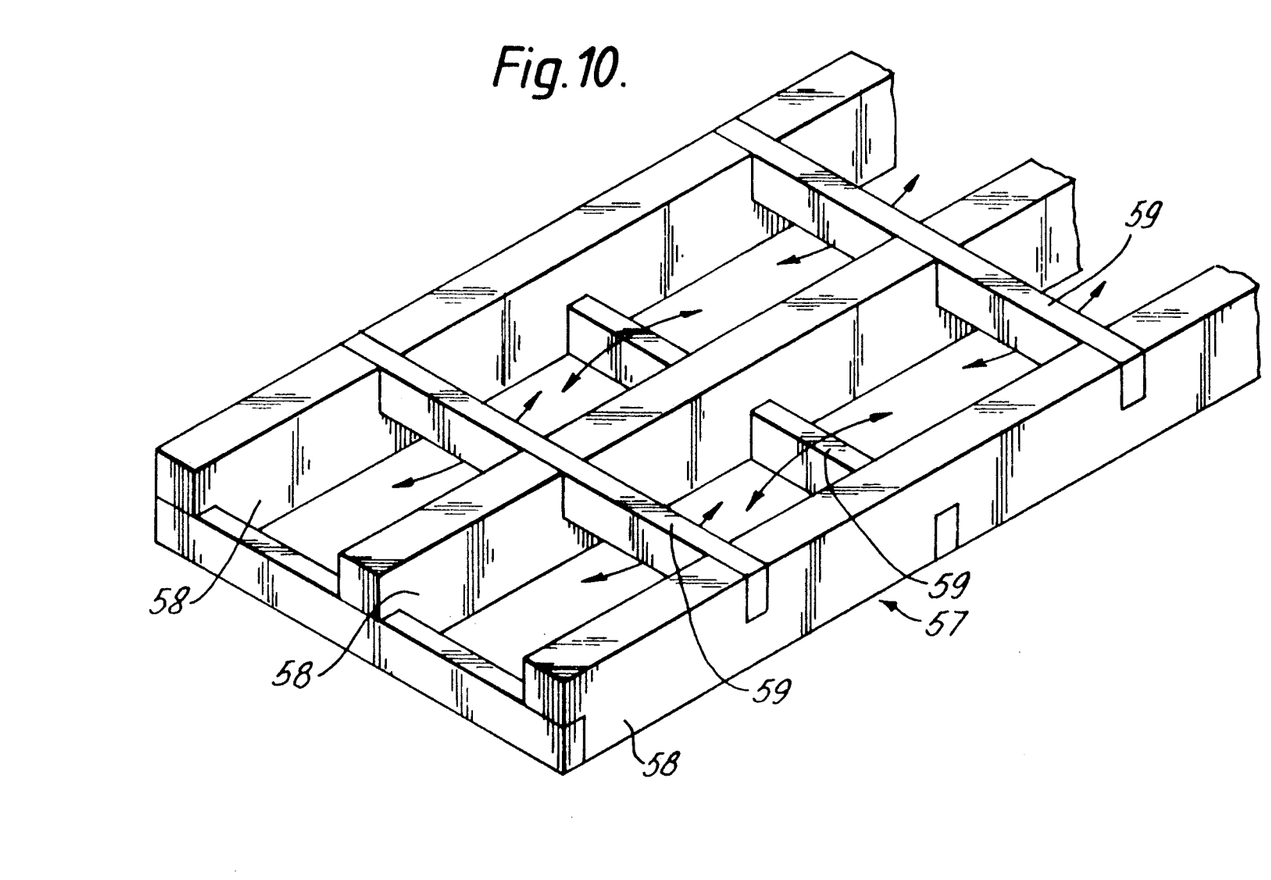
FIG. 10 is a perspective view of part of the ladder structure.

Although the corner edges of the rung deflectors at their maximum projection into the conduit are shown right angular in FIGS. 9 and 10, it may be desirable to round them as shown in FIGS. 1 to 7, to promote streamline flow past the deflectors. Similarly it might be desirable to provide fillets in the corners between the sides of the deflectors and the membranes.

For further detail of the apparatus, attention is drawn to the earlier specification WO 89/04197.

The reference letters used in FIG. 7 can be related to the critical parameters of the invention.

Aspect Ratio

This is defined as l/d, where l is the distance between deflectors and d is the gap between the membranes or other walls 50,51. A length of about two d's is needed for each vortex, so for 3 vortices $l/d \approx 6$ and for 4 vortices $l/d \approx 8$.

Thus $l/d \geq 6$.

Reynolds Number

Peak Reynolds number is defined as $$Re = \frac{\hat{u}H}{2\gamma}$$

Where H is the minimum inlet width, $\gamma$ is kinematic viscosity (about $3 \times 10^{-6} m^2 s^{-1}$ for blood) and $\hat{u}$ is peak velocity through the inlet into the chamber. In terms of peak flow rate $\hat{Q}$, for a channel of depth W (measured perpendicularly to the plane of FIG. 7), $$Re = \frac{\hat{Q}}{WH} \cdot \frac{H}{2\gamma} = \frac{\hat{Q}}{2W\gamma}$$

The preferred range is $30 < Re < 200$

Below about 30 the vortex wave does not appear, above 200 the flow is turbulent.

Strouhal Number

The Strouhal number is defined as $$St = \frac{\Omega H}{2\hat{u}}$$

Where $\Omega$ is the pulsation frequency in Hz. Thus $$St = \frac{\Omega H}{2} \cdot \frac{WH}{\hat{Q}} = \frac{\Omega W H^2}{2\hat{Q}}$$

The preferred range is $0.001 < St < 0.1$.

Figure 11:
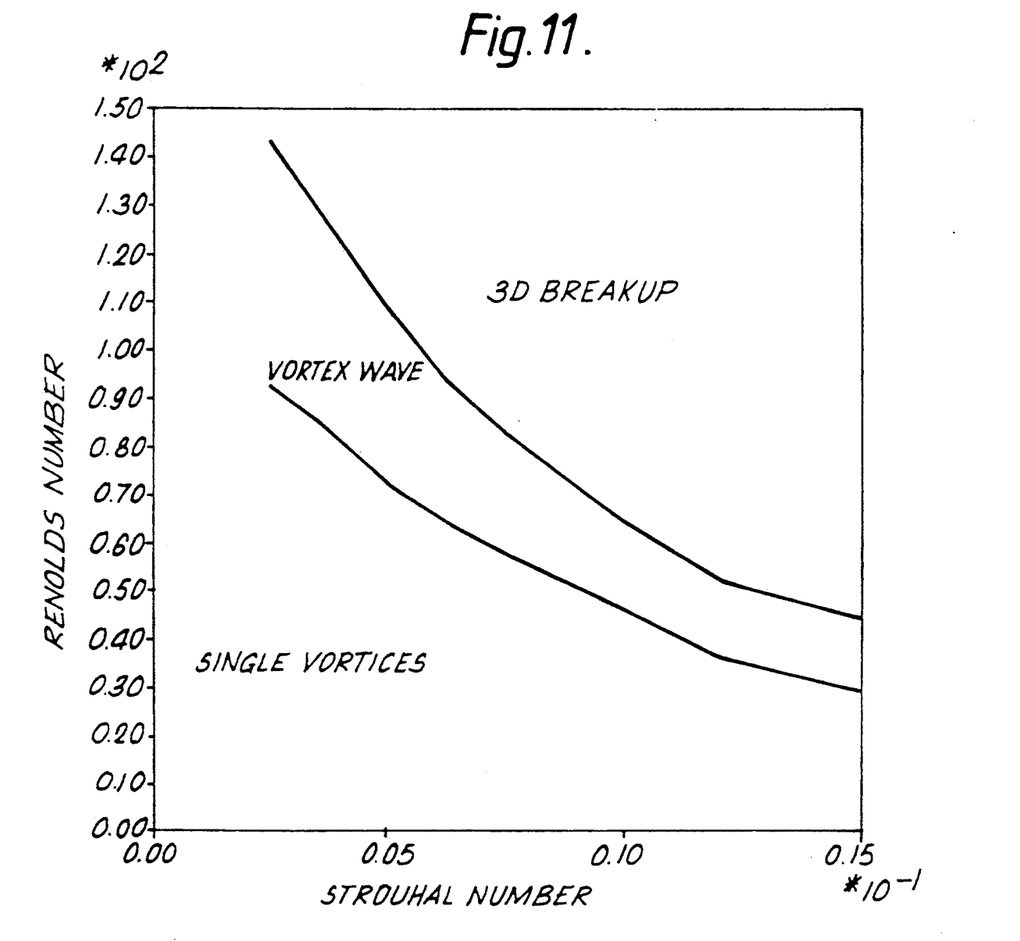
FIG. 11 is a Reynolds/Strouhal numbers map.

These conclusions are supported by the map of FIG. 11, which was prepared by experimentation with one system for the microfiltration of plasma from blood. It can be seen that best results were obtained by working within the central inclined band.

Figure 8:
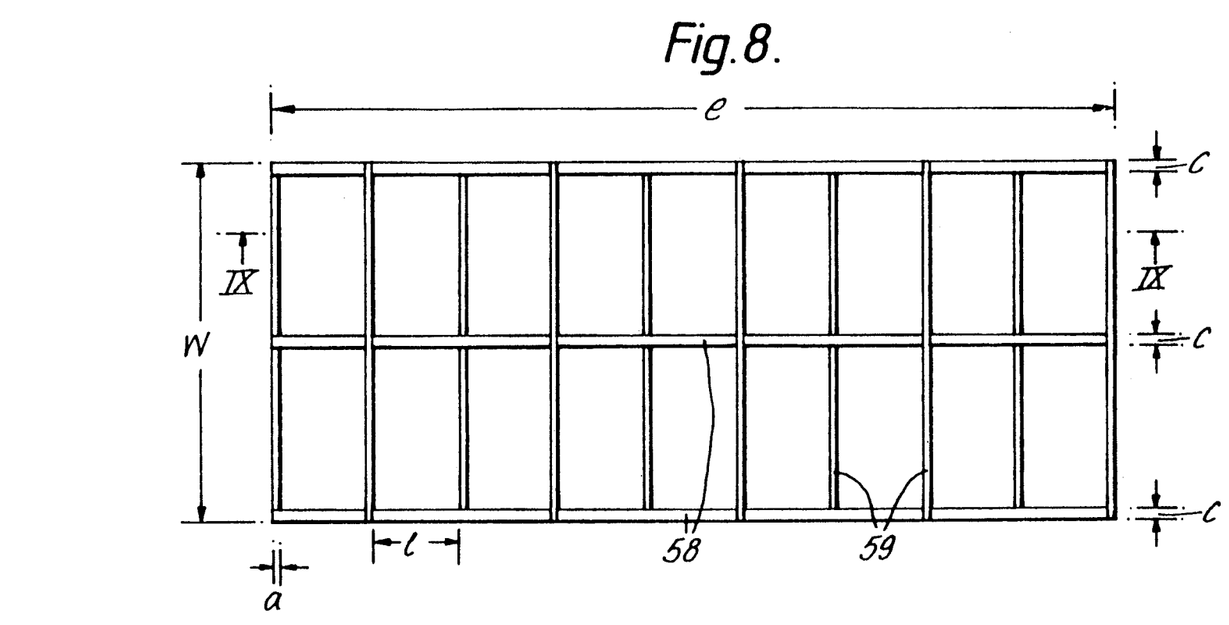
FIG. 8 is a plan of a ladder structure which may be used in the apparatus.

Utilising the apparatus of FIGS. 6 to 10, excellent results were obtained with the ultrafiltration of bovine serum albumin solutions, and the efficiency was found to be over twice that compared with conventional cross-flow ultrafiltration, utilising the same membranes. In that case the dimensions represented by the reference letters in FIGS. 7 and 8 were as follows:

a = 1 mm, b = 1 mm, c = 2 mm, d = 2 mm, e = 145 mm, H = 1 mm, l = 15 mm, W = 63 mm.

We claim:

1. A method utilizing vortices in a fluid flowing in a fluid system, wherein the fluid is passed with reversing, but means, flow through a conduit comprising at least one chamber defined by a plurality of walls including two spaced apart side walls, the chamber being provided at ends of said chamber spaced along the conduit with a restricted inlet and a restricted outlet, the Reynolds and Strouhal numbers of the fluid system, and the aspect ratio of the length of the chamber to the width of the chamber between the two walls being such that at least three vortices are set up in a standing pattern along the chamber with adjacent vortices rotating in opposite directions about axes perpendicular to the length and width of the chamber and with mainstream flow of the fluid passing along the chamber and sinuously around the vortices alternately between a vortex and different one of the walls, reversal of the flow direction reinforcing the vortices so that each continues to rotate in the same direction but with the sinuous flow now passing around each vortex and the opposite wall.

2. A method according to claim 1, wherein the aspect ratio is at least 6.

3. A method according to claim 1, wherein the Reynolds number is between 30 and 200.

4. A method according to claim 1, wherein the Strouhal number is between 0.001 and 0.1.

5. A method according to claim 1, for mixing components of the fluid, or to promote contact between the fluid and a component immobilised on a support in the chamber.

6. A method according to claim 5, wherein the aspect ratio is at least 6.

7. A method according to claim 1, for effecting transfer of heat or mass to or from the fluid, wherein at least one of the side walls is at least partly formed by a transfer membrane.

8. A method according to claim 7, wherein the aspect ratio is at least 6.

9. A method according to claim 7, wherein the Reynolds number is between 30 and 200.

10. A method according to claim 7, wherein the Strouhal number is between 0.001 and 0.1.

11. Apparatus for effecting the transfer of heat or mass using vortices in a fluid, said apparatus comprising a conduit, means for passing the fluid through the conduit with a reversing, but means, flow, said conduit including a plurality of chambers defined between at least two substantially planar side walls, each chamber having restricted opposite ends, said opposite ends respectively defining an inlet and an outlet, each of said opposite ends comprising a deflector surface which extends from one side wall, across the width of the chamber towards, but terminating short of, the opposite side wall, thereby forming the respective inlet or outlet adjacent to the opposite wall, said deflector surfaces comprising rungs of a ladder-like structure, the rungs of which are alternately offset towards opposite side walls.

12. Apparatus for effecting the transfer of heat or mass through a membrane using vortices in a fluid, said apparatus comprising a conduit, means for passing the fluid through the conduit with a reversing, but mean, flow, said conduit including a plurality of chambers defined between at least two substantially planar side walls, each chamber having restricted opposite ends, at least one of said side walls comprising a transfer membrane, said restricted opposite ends respectively defining an inlet and an outlet, each of said opposite ends comprising a deflector surface which extends from one side wall, across the width of the chamber towards, but terminating short of, the opposite side wall, thereby forming the respective inlet or outlet adjacent to the opposite wall, said deflector surfaces comprising rungs of a ladder-like structure, the rungs of which are alternately offset towards opposite side walls.

13. Apparatus for effecting the transfer of heat or mass using vortices in a fluid, said apparatus comprising a conduit, means for passing the fluid through the conduit with a reversing, but mean, flow, said conduit including a plurality of chambers defined between at least two substantially planar side walls and having restricted opposite ends, said restricted opposite ends respectively defining an inlet and an outlet, each of said opposite ends comprising a deflector surface which extends from one sidewall, across the width of the chamber towards, but terminating short of, the opposite side wall, thereby forming the respective inlet and outlet adjacent to the opposite wall, said deflector surfaces comprising elongate bars extending transverse to the direction of fluid flow in the conduit and being alternately offset towards opposite side walls.

14. Apparatus according to claim 13, wherein at least one of the side walls is a transfer membrane.

15. Apparatus according to claim 7 in which the chamber is substantially axisymmetric.

* * * * *